(12) United States Patent
Behar et al.

(10) Patent No.: US 7,684,857 B2
(45) Date of Patent: Mar. 23, 2010

(54) DEVICE FOR MEDICINE DELIVERY BY INTRAOCULAR IONTOPHORESIS OR ELECTROPORATION

(75) Inventors: Francine Behar, Paris (FR); Pierre Roy, Paris (FR)

(73) Assignee: Eyegate Pharma S.A.S., Paris (FR)

( * ) Notice: Subject to any disclaimer, the term of this patent is extended or adjusted under 35 U.S.C. 154(b) by 0 days.

(21) Appl. No.: 10/492,487

(22) PCT Filed: Oct. 11, 2002

(86) PCT No.: PCT/FR02/03473

§ 371 (c)(1), (2), (4) Date: Oct. 25, 2004

(87) PCT Pub. No.: WO03/043689

PCT Pub. Date: May 30, 2003

(65) Prior Publication Data

US 2005/0049541 A1 Mar. 3, 2005

(30) Foreign Application Priority Data

Oct. 12, 2001 (FR) .................................. 01 13177

(51) Int. Cl.
*A61N 1/30* (2006.01)

(52) U.S. Cl. ...................................................... 604/20

(58) Field of Classification Search ................... 604/20, 604/294
See application file for complete search history.

(56) References Cited

U.S. PATENT DOCUMENTS

| | | | | |
|---|---|---|---|---|
| 4,564,016 A | * | 1/1986 | Maurice et al. | 604/20 |
| 5,331,950 A | * | 7/1994 | Wood, Sr. | 600/109 |
| 5,669,874 A | * | 9/1997 | Feiring | 604/21 |
| 5,725,514 A | * | 3/1998 | Grinblat et al. | 604/294 |
| 6,001,088 A | * | 12/1999 | Roberts et al. | 604/501 |
| 6,101,411 A | | 8/2000 | Newsome | |
| 6,154,671 A | * | 11/2000 | Parel et al. | 604/20 |
| 6,299,307 B1 | * | 10/2001 | Oltean et al. | 351/210 |

FOREIGN PATENT DOCUMENTS

EP  1127586  8/2001

* cited by examiner

*Primary Examiner*—Nicholas D Lucchesi
*Assistant Examiner*—Christopher D Koharski
(74) *Attorney, Agent, or Firm*—Foley & Lardner LLP; Michel Morency; James F. Ewing

(57) ABSTRACT

The invention concerns a device for ocular delivery of an active principle by peroperative intraocular iontophoresis or electroporation comprising a reservoir (7) for receiving a solution comprising the active principle, means for diffusing (8, 6) the active principle connected to the reservoir, means for injecting (4) the solution into the reservoir, and means (5) for exerting suction of the content of the reservoir during an injection of the solution therein by the injection means.

21 Claims, 3 Drawing Sheets

Figure 5A:
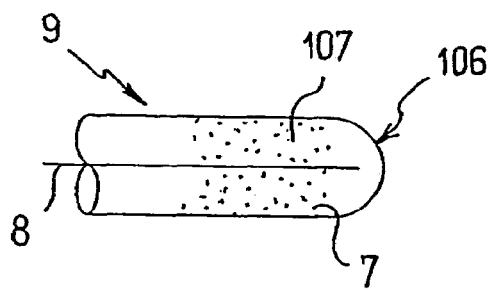

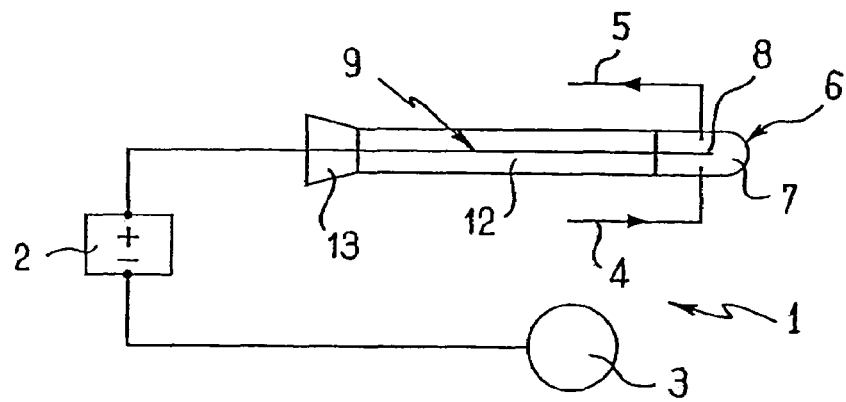
FIG.1
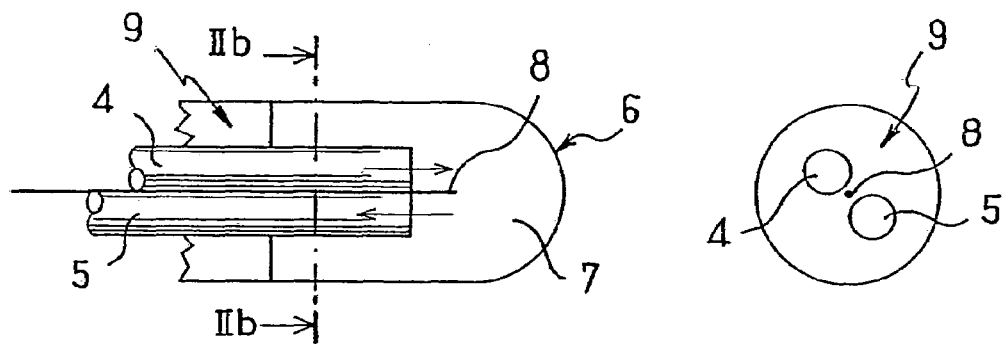 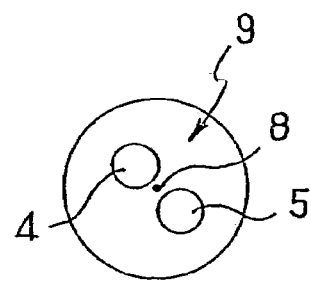
FIG.2a   FIG.2b
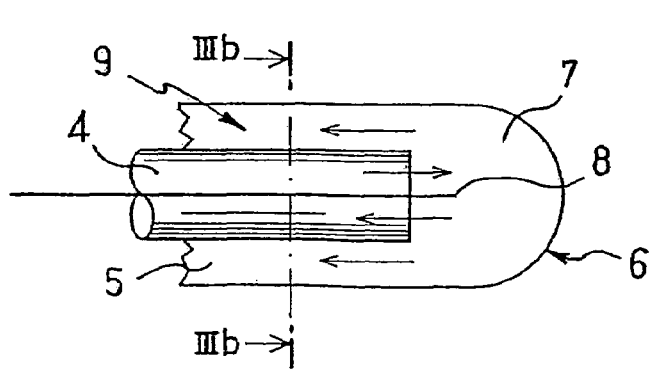 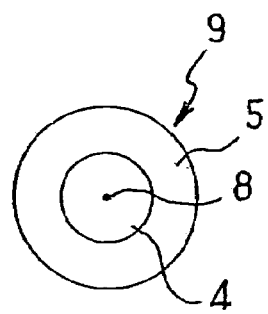
FIG.3a   FIG.3b
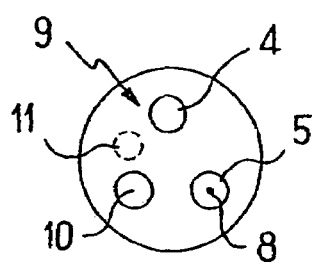
FIG.4

DEVICE FOR MEDICINE DELIVERY BY INTRAOCULAR IONTOPHORESIS OR ELECTROPORATION

The invention relates to a device for applying an active principle by iontophoresis or electroporation, intended for eye treatment so as to improve the intraocular delivery of active principles in ophthalmology.

Iontophoresis, like electroporation, uses electric current to allow the diffusion of a charged molecule through a biological membrane. The permeability of the biological membrane is increased under the effect of the electric current, thereby allowing the passage of larger molecules, and the electric field pushes the molecules through this membrane.

At present, existing ocular iontophoresis devices are periocular devices. The document U.S. Pat. No. 4,564,016 discloses such a device which comprises a balloon mounted on the distal end of a probe. This balloon makes it possible to clear the retrobulbar space (behind the eye). Such a device has the major disadvantage of pressurizing the eye, the normal pressure of which is 18 mmHg. Above 21 mmHg, the risk of acute glaucoma due to a sudden increase in ocular pressure is high, this glaucoma leading to loss of vision on account of the optic nerve being damaged.

On the other hand, the use of this type of device causes pressure in the periocular (retrobulbar and peribulbar) spaces. This pressure may lead to poor blood flow on account of compression at the head of the optic nerve. In some cases, this may go as far as venous or arterial occlusion leading to a partial or total loss of vision.

Another drawback due to such a device is that the wall of the ocular globe is thick at this point. Moreover, this device does not make it possible to precisely target the cells or the organs of the eye, and the surface area treated is large. This does not make it possible to provide correct and optimal treatment of an intraocular target that is to be treated, such as cells of the retina for example.

It is an object of the invention to provide a device for applying an active principle by intraocular iontophoresis or electroporation which makes it possible to precisely target the zone that is to be treated while avoiding the risk of glaucoma.

For this, there is provided according to the invention a device for the ocular application of an active principle by peroperative intraocular iontophoresis or electroporation, comprising a reservoir that can receive a solution comprising the active principle and diffusion means for diffusing the active principle, said diffusion means being connected to the reservoir, the device also comprising injection means for injecting the solution into the reservoir and means that can suck up the contents of the reservoir during injection of the solution into the latter by the injection means.

Thus, the presence of injection means (e.g., injection tube) coordinated with suction means (e.g., suction tube) makes it possible to maintain:

a constant and defined pressure within the reservoir, a constant and defined volume if the reservoir can be deformed.

This is compatible with introducing the reservoir into the ocular globe without substantially increasing the pressure of the globe. This avoids the risk of glaucoma and makes it possible to precisely approach the target cells that are to be treated and to treat only the latter, without there being any diffusion of active principle into the entire ocular space.

Advantageously, the device has at least one of the following characteristics:

the device comprises an injection tube and a suction tube which extend inside one another and can be connected to the reservoir, the diffusion means are arranged at a distal end of a probe, the reservoir is arranged at the distal end, the device comprises an injection tube and a suction tube which extend into a probe, the distal end of the probe forms an angle with respect to the direction along which the probe mainly extends, the angle is between 90° and 170°, thus allowing contact with the retina while maintaining optimum visibility for manipulation through the crystalline lens, the angle is around 135°, an iontophoresis or electroporation electrode extends in a probe, in particular inside the reservoir, the diffusion means comprise a porous wall that can allow the active principle through, in particular under the effect of an iontophoresis or electroporation current, the reservoir has a wall that comprises at least one diffusion orifice, the orifice is covered with a permeable or semi-permeable membrane that can allow the active principle through, in particular under the effect of an iontophoresis or electroporation current, the lateral orifice is plugged on the reservoir side by a stopper which is made of absorbent material that can allow the active principle through, in particular under the effect of an iontophoresis or electroporation current, the device also comprises an optical fiber that can be connected to a light source and arranged so as to illuminate the environment of the diffusion means, in particular of the target cells that are to be treated, the device comprises a second optical fiber that can be connected to a camera and arranged so as to record images of the environment of the diffusion means, in particular of the target cells that are to be treated.

There is also provided, according to the invention, a probe for the ocular application of an active principle by intraocular iontophoresis or electroporation, comprising a reservoir that can receive a solution comprising the active principle and diffusion means for diffusing the active principle, said diffusion means being connected to the reservoir, the probe also comprising an injection tube for injecting the solution into the reservoir and a suction tube for sucking up the contents of the reservoir.

There is also provided, according to the invention, a surgical method that can make use of the device having at least one of the aforementioned characteristics, which method comprises at least one of the following steps:

placement of a return electrode, which is connected to a generator, onto the tissues neighboring the ocular globe that is to be treated, the return electrode is an electrode of the cutaneous type, the return electrode can be positioned on all or part of the external surface of the ocular globe, incision of the sclera of the ocular globe that is to be treated, introduction, via the incision, of the probe into the vitreous body, positioning of the distal end of the probe in the vicinity of the zone of the ocular globe that is to be treated, injection into the reservoir, by the injection means, of a solution comprising the active principle and regulation of the pressure and/or volume of the reservoir by way of the suction means, charging of the electrode of the probe, which is connected to the generator, for a given time and for a given voltage, stopping of the generator, withdrawal of the probe and of the return electrode,
closing of the incision in the sclera.

Figure 5B:
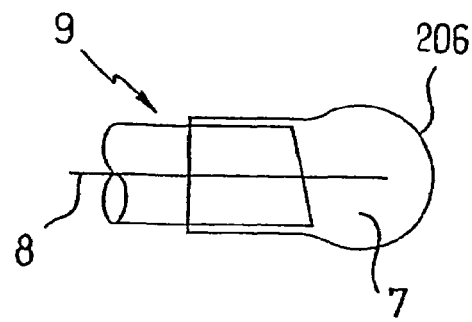
Figure 5C:
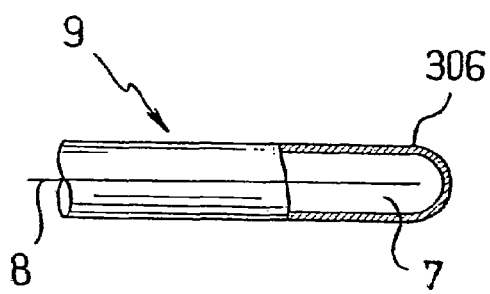
Figure 5D:
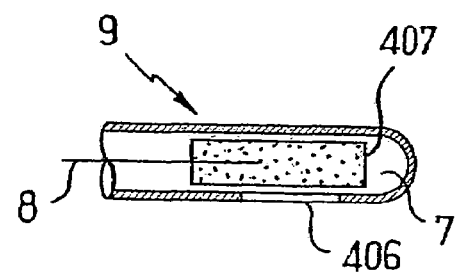
Figure 5E:
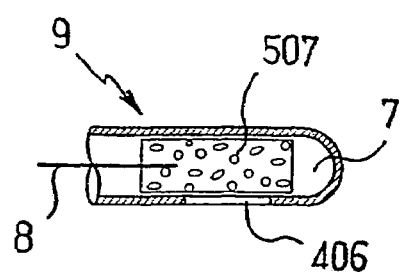
Figure 6:
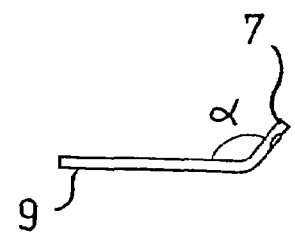
Figure 7:
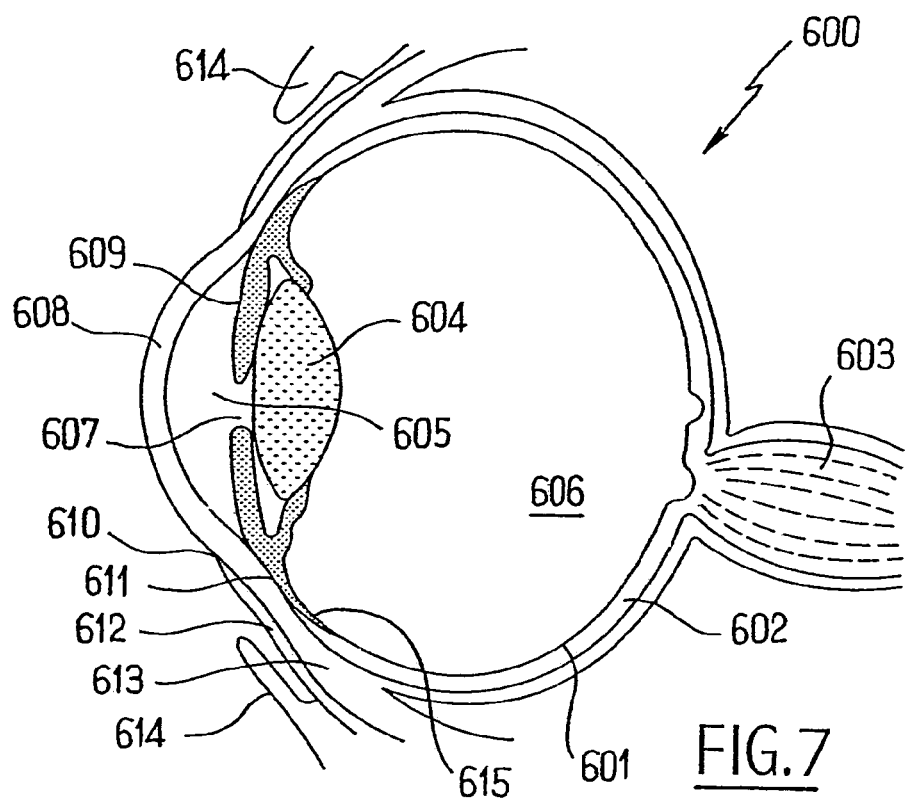
Figure 8:
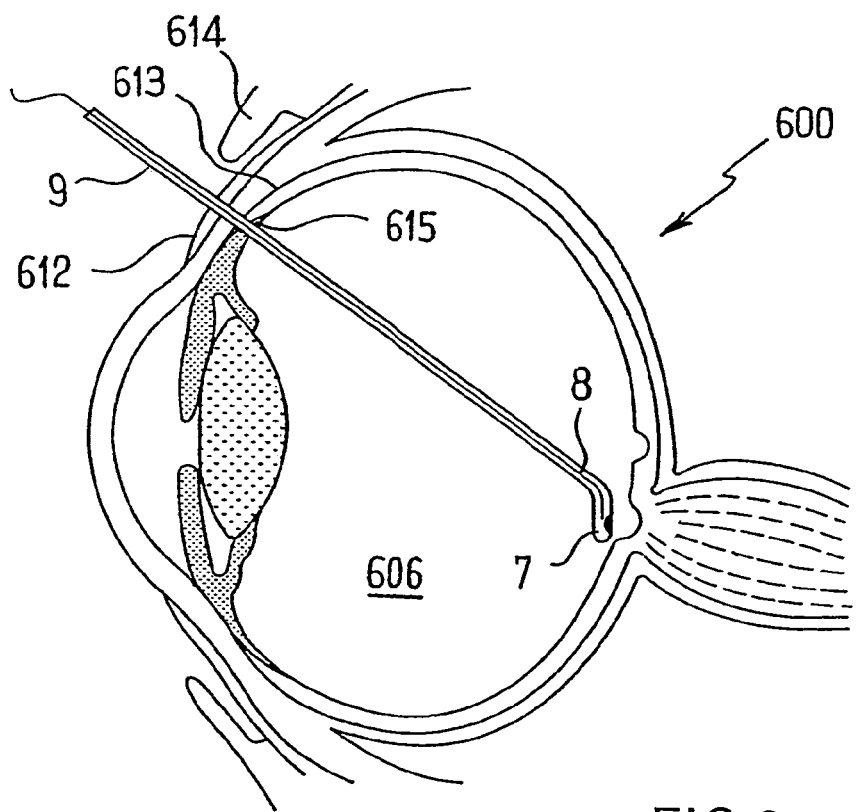

Other characteristics and advantages of the invention will become apparent from the following description of a preferred embodiment and of variants. In the attached drawings:

FIG. 1 is a schematic representation of an intraocular application device according to the invention, FIG. 2a is a partial view of the distal end of a probe according to a first embodiment of the invention, FIG. 2b is a section on IIb-IIb of the distal end of the probe of FIG. 2a, FIG. 3a is a partial view of the distal end of the probe according to a second embodiment of the invention, FIG. 3b is a view in section on IIIb-IIIb of the distal end of the probe of FIG. 3a, FIG. 4 is a view in section of the distal end of a probe according to a third embodiment of the invention, FIGS. 5a to 5e are different embodiments of the distal end and of the reservoir of a probe according to the invention, FIG. 6 shows a probe according to a variant embodiment of the invention, FIG. 7 is an anatomical section of an ocular globe, and FIG. 8 is an anatomical section of the ocular globe showing the insertion during use of a probe according to the invention.

With reference to FIG. 1, a description will be given of a device for the ocular application of an active principle by intraocular iontophoresis or electroporation according to the invention. The device 1 comprises a current generator 2 which is connected to a first electrode 3, known as the return electrode, and to a second electrode 8, known as the main electrode or active electrode. A reservoir 7 is associated with this main electrode 8, which reservoir can receive the active principle that is to be applied or else a solution comprising the active principle. The reservoir 7 comprises injection means 4 and suction means 5. Moreover, the reservoir comprises a porous wall 6 that can allow the active principle through only during iontophoresis or electroporation. The reservoir 7 may be mounted on a probe 9. Preferably, the reservoir is situated at the distal end of the probe 9.

The return electrode 3 is designed to close the electrical circuit formed by the generator, the main electrode and the organic tissues. The electrode 3 is placed opposite the main electrode 8 and the organic tissues that are to be treated or else preferably in the near vicinity of these tissues that are to be treated, as will be seen below. In this case, the return electrode 3 is a cutaneous electrode of the TENS type (Transcutaneous Electrical Nerve Stimulation). It is mainly composed of a conductive skin adhesive and of a conductive carbon film that is connected to the generator by an electrical wire.

The main electrode 8 is preferably made of a material chosen from a wide range of electrically conductive materials. These materials may be:

inert. They do not corrode electrochemically on account of the presence of the electric current during operation of the device. These inert materials are stainless steel, platinum, gold, carbon, tungsten, etc.

sacrificial. They are converted, under the action of the electric current during operation of the device, into metal ions which precipitate, avoiding electrolysis of the solution comprising the active principle. These materials are silver, copper, etc.

According to other variant embodiments, the main electrode 8 consists of ink or of conductive polymer, or else of conductive particles dispersed in a matrix.

Moreover, the main electrode 8 is in the form of a wire, a film, a plate or even a woven material.

The current generator 2 supplies a DC current having an intensity of between about 0.5 and 5 mA, for a period ranging from about 0.5 to 10 minutes. Depending on the resistance of the organic tissues involved in the circuit, which resistance may vary during iontophoresis, the current supplied by the generator 2 adapts according to Ohm's law U=R.I, where U is the current in Volts, R is the resistance in Ohms and I is the intensity in Amps; however, the current supplied by the generator 2 can never exceed 20 V.

According to one variant embodiment, the generator 2 may be an AC current generator. The AC current has the advantage of avoiding variation of the pH on account of oxidoreduction phenomena at the main electrode. The frequency range of this AC current is chosen so as to allow optimal permeability of the tissues that are to be treated. In this case, the return electrode 3 is preferably an electrode of the ECG type (ElectroCardioGram) and is composed of a skin adhesive and of an Ag/AgCl film having a very low impedance.

According to another variant embodiment, the generator 2 may supply a current profile having voltage peaks which are very high between about 50 and 2500 V, and of very short duration, between about 0.01 and 0.1 s, at a very low intensity. This type of profile is usually used in electroporation.

The probe 9 comprises, in this case, three main parts: a connection socket 13, a tube 12 and a distal end 7 comprising the reservoir 7. The connection socket 13 is of the female Luer type which is the universal standard for connection of intravenous catheters. This socket has the general shape of a cone having an inlet diameter of around 4 mm and a conicity of around 6%. The tube of the probe is made of a biocompatible polymer material, preferably such as polyvinyl chloride, polyethylene, polypropylene, polyamide, polyether block amide, polyurethane or silicone, depending on the desired hardness and transparency characteristics.

With reference to FIGS. 2a and 2b, a description will be given of a first embodiment of the probe 9. The probe 9 comprises an injection tube 4 that opens into the reservoir 7 located at the distal end of the probe 9. This tube 4 travels along the probe 9 essentially parallel to a longitudinal axis of said probe. Likewise, a suction tube 5 travels essentially parallel to the tube 4 within the probe 9 and plunges into the reservoir 7. As shown in FIG. 2b, the probe is preferably of circular cross section, as are the tubes 4 and 5. The diameter of this circular cross section is between about 0.9 mm (gauge 20) and about 2.1 mm (gauge 14). The length of the probe 9 is between about 20 and 50 mm.

With reference to FIGS. 3a and 3b, a description will be given of a second embodiment of the probe 9. The probe 9, as above, has an injection tube 4 that opens into the reservoir 7 located at the distal end of the probe. The tube 4 has a longitudinal axis that is almost coincident with a longitudinal axis of the probe 9. The latter acts as a suction tube 5. The electrode 8 is located essentially along the longitudinal axis of the tube 4 and of the probe 9. The probe 9 and the tube 4 preferably have a circular cross section. The electrode 8, the injection tube 4 and the probe 9 are thus essentially coaxial.

With reference to FIG. 4, a description will be given of a third embodiment of the probe 9. As shown in this figure, the probe 9 has a circular cross section. Within this probe 9 there travel, in a manner essentially parallel to a longitudinal axis of the probe 9, an injection tube 4 of preferably circular cross section and a suction tube 5 of preferably circular cross section, in which the electrode 8 is located. Moreover, the probe 9 has a first optical fiber 10 which is connected to a light source (not shown) so as to guide light rays into the vicinity of the distal end of the probe 9 to illuminate the environment of the target that is to be treated. Finally, the probe 9 may have a second optical fiber 11 which is connected to a camera and can guide toward this camera light rays coming from the distal end of the probe so as to make the camera record images of the environment of the target that is to be treated. The presence of these optical fibers makes it possible to improve the precision with which the probe will be manipulated to treat the target by iontophoresis or electroporation.

With reference to FIGS. 5a to 5e, a description will be given of different embodiments of the wall of the reservoir.

With reference to FIG. 5a, the wall 106 of the reservoir 7 has a multitude of micro-orifices 107 passing through the wall 106. These micro-orifices 107 can allow the molecules of the active principle through, under the action of the electric field emitted by the electrode 8, which makes it possible to carry out iontophoresis or electroporation. Preferably, the various micro-orifices 107 are uniformly distributed over a strip surrounding the reservoir, the width of which strip does not exceed the size of the reservoir. More preferably, various micro-orifices are located on a limited portion of the wall of the reservoir. The micro-orifices have a mean diameter of between about 0.01 and 0.1 mm.

With reference to FIG. 5b, the probe 9 is open at its distal end 9 and a balloon 206 is slipped over the open distal end of the probe 9, the balloon acting as reservoir 7. The membrane forming the balloon 206 is a preferably semi-permeable or permeable or even micro-porous membrane that can allow the molecules of the active principle through only under the action of the electric field generated by the electrode 8 during iontophoresis or electroporation.

In FIG. 5c, the distal end of the probe 9 has a porous end-piece 306 surrounding the reservoir 7. The porous end-piece can allow the molecules of the active principle through only under the effect of the electric field generated by the electrode 8 during iontophoresis or electroporation.

In FIG. 5d, the distal end of the probe 9 has an orifice 406 that can allow the reservoir 7 to communicate with the exterior of the probe. Preferably, the orifice 406 is located on a lateral wall surrounding the reservoir 7. This orifice 406 is plugged by a preferably permeable or semi-permeable or even micro-porous membrane 407. This membrane 407 may be located on the orifice 406 inside the reservoir 7 or else positioned on the orifice 406 outside the reservoir 7. Preferably in this case, the membrane may be a sleeve that is slipped over the distal end of the probe and covers the orifice 406. The through-orifice is made by a piercing with a mean diameter of between about 0.5 and 1 mm. The membrane has a porosity of between about 1 and 10 μm.

In FIG. 5e, the end of the probe 9 has the same end configuration as that shown in FIG. 5d. In this case, the orifice 406 is plugged by an absorbent material 507 which takes up the majority of space in the reservoir 7. The absorbent material 507, like the membrane 407, can allow the molecules of the active principle through only under the effect of an electric field coming from the electrode 8 during iontophoresis or electroporation. The absorbent material is preferably foam or sponge.

In all the embodiments of the probe 9 described above, the main electrode 8 must be placed opposite either the membrane or the orifices so as to allow an optimal flow of the electric current to the outside of the probe 9 during operation.

Moreover, according to the embodiments described above, the effective treatment surface area of target cells is between about 50 μm in diameter and about 2 mm in diameter.

With reference to FIG. 6, the probe may be bent at its distal end. The angle α that the distal end forms with the tube 12 of the probe may be between 90° and 170°. Preferably, this angle is more or less equal to 135°. The choice of this angle of 135° depends on the route used to introduce the probe into the ocular globe, as will be seen below. The angle is chosen so that the longitudinal axis of the distal end of the probe 9 is essentially parallel to the surface formed by the target cells that are to be treated. In one variant embodiment (not shown), the angle that the distal end of the probe forms with the tube of the probe is chosen by the operator during the surgical procedure, so as to perfect the previous alignment. For this, the distal end of the probe 9 comprising the reservoir 7 is mounted to rotate, about an axis (not shown) that is perpendicular to the axis along which the probe mainly extends, on the tube of the probe 9, and the application device comprises means for using this end that are located at the proximal end of said probe.

A description will now be given of the use in practice of the device for application by intraocular iontophoresis or electroporation according to the invention.

With reference to FIG. 7, the eye 600 has the overall shape of a balloon. The anterior part of the wall consists of a transparent cornea 608 behind which there is a pupil 607. The latter is separated from the cornea 608 by an anterior chamber 605 comprising an aqueous humor. The pupil is closed by a transparent crystalline lens 604 which is shaped in the manner of a convergent lens. The volume 606 located behind the crystalline lens 604 is called the vitreous body. The posterior wall of the eye consists of a first layer 601 which forms the functional retina, then of a second layer 602 called the choroid and then finally of a third layer 613 called the sclera. At the rear end of the ocular globe there is an optic nerve 603. The crystalline lens 604 is kept at the front by an iris 609 and is connected to the wall of the ocular globe at the limit between the cornea and the sclera by a ciliary body 611. Between the point of attachment of the ciliary body 611 and the start of the functional retina 601 there is a non-functional pars plana 615. From a limb 610 surrounding the cornea 608, there is a layer of tissue 612, known as conjunctive tissue, extending above the sclera up to the point of implantation of the eyelids 614.

With reference to FIG. 8, a description will be given of the mode of operation. The surgeon undertakes a transcleral route by making an incision in the sclera at the non-functional pars plana 615. This is because the wall forming the ocular globe is least thick at this particular point. Next, the surgeon positions the electrode 3 of the application device 1 on the skin of the face as close as possible to the eye, preferably on the forehead, the cheek or the eyelid (it is also possible to position the return electrode under the conjunctive tissue, in direct contact with the ocular globe, or even directly into the eye). Next, he introduces, via the incision made in the sclera, the probe 9 which then penetrates into the vitreous body 606. The surgeon, has the possibility of monitoring the introduction of the probe either directly through the cornea and the crystalline lens, which are transparent, or else with the aid of a camera if the probe is equipped with an optical fiber for this purpose, or else with the aid of a slot lamp or a lens. The introduction of the probe 9 is carried out such that the curved distal end 7 comes into the vicinity of the cells that are to be treated. Once the probe 9 has been put in place, the surgeon makes a current flow into the electrode 8 so as to carry out iontophoresis or electroporation, during which a certain amount of active principle, depending on the intensity of the current on the one hand and the time for which current is supplied on the other, is transferred from the reservoir 7 into the target cells that are to be treated. Next, the surgeon withdraws the probe 9 and then closes his incision.

As has been seen, the configuration of the probe 9 and the route used make it possible to apply the active principle in a very localized manner, without affecting the tissues that are not to be treated.

The main indication for the use of the application device 1 is retinal vessel occlusion, a classic cause of total or partial loss of vision, particularly in elderly people. It is also one of the complications of diabetic retinopathies.

There are two forms of retinal vessel occlusion:
the ischemic form, which is the rarest (10% to 15% of cases), is manifested by a sharp drop in visual sharpness, evolving toward neovascularization and glaucoma,
the edematous form, which is the most frequent (60% to 80% of cases), is manifested by a visual haze, and evolves either toward remission in the case of young patients or toward a chronic form with slow degradation of the retina or finally toward the ischemic form described above.

Vessel occlusion is considered an emergency and is currently treated by fibrinolytic treatments (thrombolysis or dissolution of the clots) by the general or local route, or by rheological treatments (removal of a certain amount of blood) by the general route, or else by laser photocoagulation treatments which make it possible to prevent or regress neovascularization on the one hand and to combat macular edema on the other. The case of injecting fibrinolytics by the general route presents significant hemorrhagic complications. In the case of injecting these same fibrinolytics by the local route (that is to say via the vitreous body), the occurrence of intraocular hemorrhages is observed. Thus, the device for application by iontophoresis or electroporation 1 according to the invention allows the injection of these same fibrinolytics onto the sole target tissue that is to be treated, while avoiding the hemorrhagic complications described above.

Other ocular pathologies may be treated by a device for application by iontophoresis or electroporation according to the invention. These include degenerative diseases of the retina that are linked with age and also diabetic retinopathies in general. Many molecules are being developed to slow down or even halt the neovascularization observed in these pathologies. These molecules may be injected using a device according to the invention. This makes it possible to increase the local concentrations of these medicaments on the one hand and on the other hand to be able to pass larger molecules into the target tissues, such as for example during a localized administration of antimitotics or of antiangiogenics.

Likewise, the device according to the invention may be used for the transfection by iontophoresis or electroporation of plasmids or of medicaments for gene therapy (such as for example of chimeric or antisense oligonucleotides, or else ribozymes), the main mode of action of which is to correct genes or fragments of genes inside the target cells.

Of course, many modifications may be made to the invention without thereby departing from the scope thereof.

The invention claimed is:

1. A device for an ocular application of an active principle by peroperative intraocular iontophoresis or electroporation within an ocular globe of an eye, comprising:
a reservoir arranged for being at least partly introduced into the ocular globe, close to cells to be treated, the reservoir receiving a solution comprising the active principle;
means for injecting the solution into the reservoir;
means for sucking up contents of the reservoir during injection of the solution into the reservoir by the injection; and
a porous reservoir wall of the reservoir, the porous reservoir wall being folly introduced into the ocular globe, at least a portion of which is configured to provide porous access to the reservoir, the porous access configured to allow molecules of the active principle to pass through the porous reservoir wall only under the effect of an electric field.

2. The device as claimed in claim 1, wherein the means for injecting comprising an injection tube and the means for sucking comprising a suction tube, the injection tube and the suction tube extend inside one another and can be connected to the reservoir.

3. The device as claimed in claim 1, wherein the reservoir is arranged at a distal end of a probe.

4. The device as claimed in claim 3, wherein the distal end of the probe forms an angle ($\alpha$) with respect to the direction along with the probe mainly extends.

5. The device as claimed in claim 4, wherein the angle is between 90° and 170°.

6. The device as claimed in claim 5, wherein the angle is around 135°.

7. The device as claimed in claim 3, wherein the porous reservoir wall includes a porous end-piece positioned at a distal end of the probe surrounding the reservoir.

8. The device as claimed in claim 1, comprising an injection tube and a suction tube which extend into a probe.

9. The device as claimed in claim 1, wherein an iontophoresis or electroporation electrode extends in a probe, the reservoir being arranged at a distal end of the probe.

10. The device as claimed in claim 1, wherein the porous reservoir wall comprises a plurality of micro-orifices passing through the wall.

11. The device as claimed in claim 1, wherein at least a portion of the porous reservoir wall comprises a balloon having a semi-permeable membrane.

12. The device as claimed in claim 1, wherein the porous reservoir wall defines an orifice, the device including a porous membrane positioned to plug the orifice and provide porous access to the reservoir.

13. The device as claimed in claim 1, further comprising an optical fiber that can be connected to a light source and arranged so as to illuminate the environment of the diffusion means, in particular of the target cells that are to be treated.

14. The device as claimed in claim 13, comprising second optical fiber that can be connected to a camera and arranged so as to record images of the environment of the diffusion means, in particular of the target cells that are to be treated.

15. The device as claimed in claim 1, wherein the porous reservoir wall defines an orifice, the device including an absorbent material positioned to plug the orifice and provide porous access to the reservoir.

16. The device as claimed in claim 1, wherein the at least a portion of the porous reservoir wall providing porous access comprises a one or more micro-orifices having a mean diameter of between about 1 µm and about 10 µm.

17. A probe for an ocular application of an active principle by intraocular iontophoresis or electroporation within an ocular globe of an eye, comprising:
a reservoir arranged for being at least partly introduced into the ocular globe, close to cells to be treated, the reservoir receiving a solution comprising the active principle; an injection tube for injecting the solution into the reservoir;
a suction tube for sucking up the contents of the reservoir; and
a porous reservoir wall of the reservoir, the porous reservoir wall being fully introduced into the ocular globe, at least a portion of which is configured to provide porous access to the reservoir, the porous access configured to allow molecules of the active principle to pass through the porous reservoir wall only under the effect of an electric field.

18. The device as claimed in claim 17, wherein the at least a portion of the porous reservoir wall providing porous access comprises a one or more micro-orifices having a mean diameter of between about 1 µm and about 10 µm.

19. The device as claimed in claim 17, wherein the porous reservoir wall comprises a plurality of micro-orifices passing though the wall.

20. The device as claimed in claim 19, wherein the micro-orifices have a mean diameter of between about 0.01 mm and 0.1 mm.

21. A device for an ocular application of an active principle by peroperative intraocular iontophoresis or electroporation, comprising:

a probe having proximal end and a distal end, comprising:
    a reservoir at the distal end for receiving a solution comprising the active principle;
    at least two fluid channels in fluid communication with the reservoir; and
    an electrode disposed with the probe configured to create an electric field for applying the active principles to an ocular component of an eye;

at least one of the fluid channels configured to deliver the active principles to the reservoir; and at least another fluid channel configured to remove contents from the reservoir during the delivery of the active principles.

* * * * *